United States Patent
Pitha

(10) Patent No.: US 6,602,860 B1
(45) Date of Patent: Aug. 5, 2003

(54) CRYSTALLINE MIXTURES OF PARTIAL METHYL ETHERS OF BETA-CYCLODEXTRIN AND RELATED COMPOUNDS

(76) Inventor: Josef Pitha, P.O. Box 127, Deal Island, MD (US) 21821

( * ) Notice: Subject to any disclaimer, the term of this patent is extended or adjusted under 35 U.S.C. 154(b) by 27 days.

(21) Appl. No.: 09/708,622

(22) Filed: Nov. 9, 2000

Related U.S. Application Data

(60) Provisional application No. 60/164,949, filed on Nov. 12, 1999.

(51) Int. Cl.[7] ................ A61K 31/715; A01N 43/04; C08B 37/16
(52) U.S. Cl. ................ 514/58; 536/103; 210/651
(58) Field of Search .............. 514/58; 536/103; 210/651

(56) References Cited

U.S. PATENT DOCUMENTS 4,746,734 A * 5/1988 Tsuchiyama et al. ....... 536/103
4,933,948 A * 6/1990 Herkstroeter ................ 372/53
5,472,954 A * 12/1995 Loftsson ...................... 514/58
5,698,535 A * 12/1997 Geczy et al. ................. 514/58

OTHER PUBLICATIONS

Takeo et al, "Selective Chemical Modification of Cyclomalto–Oligosaccharides via tert–Butyldimethylsilylation", Carbohydrate Research, vol. 187, pp. 203–221 (1989).*
Irie et al, "Alkylation of Cyclomalto–Oligosaccharides (Cyclodextrins) with Dialkyl Sulfate–Barium Hydroxide: Heterogeneity of Products and the Marked Effect of the Size of the Macrocycle", Carbohydrate Research, vol. 192 (1989), pp. 167–172.*

* cited by examiner

Primary Examiner—James O. Wilson
Assistant Examiner—Everett White
(74) Attorney, Agent, or Firm—Glenna Hendricks

(57) ABSTRACT

Certain mixtures of cyclodextrin derivatives, which were synthesized in mildly basic conditions, can be separated into mixtures that crystallize easily and mixtures of similar composition, which remain amorphous. Thus, it is possible to obtain the particular advantages of crystalline and/or amorphous state components from one reaction product. Both crystalline and amorphous components of the product have good ability to form inclusion complexes.

16 Claims, No Drawings

CRYSTALLINE MIXTURES OF PARTIAL METHYL ETHERS OF BETA-CYCLODEXTRIN AND RELATED COMPOUNDS

CROSS-REFERENCE TO RELATED APPLICATIONS

This application takes priority from provisional patent application 60/164,949 filed Nov. 12, 1999.

FIELD OF INVENTION

This invention relates to mixtures of partial ethers of cyclodextrins that have the ability to crystallize and the use of these mixtures to solubilize and stabilize other compounds.

BACKGROUND OF THE INVENTION

Cyclodextrins are a group of compounds consisting of, or derived from, alpha-, beta- and gamma-cyclodextrins, so called parent cyclodextrins. Alpha-, beta- and gamma-cyclodextrin are crystalline oligosaccharides consisting of six, seven or eight glucose residues, respectively, with residues connected by 1 to 4 alpha glycosidic bonds to form a macrocycle. Cyclodextrins have the ability to include other compounds into their macrocycles. No chemical bonds are formed in this process, called formation of inclusion complexes. Cyclodextrins function as hosts, while the included compounds are called guests. Inclusion complexes formed by cyclodextrins have been useful for solubilizing and stabilizing guests such as drugs, ingredients of cosmetic and personal care products, dyes, agricultural chemicals and inorganic nanoparticles.

To improve the ability to form inclusion complexes, parent cyclodextrins have to be converted to derivatives. Each glucose residue of a cyclodextrin has one primary (OH-6) and two secondary (OH-2 and OH-3) hydroxyls that can be substituted (for example, converted into ethers). The final product obtained by such reactions can be either chemically distinct cyclodextrin derivatives, or mixtures whose components are partially etherified cyclodextrins that differ in number and position of substituents.

Known mixtures of cyclodextrin derivatives exist in stable, noncrystalline (that is, amorphous) form. Partial methyl ethers of cyclodextrins synthesized under strongly basic conditions provide widely used amorphous mixtures (U.S. Pat. No. 5,710,268; World Intellectual Property Organization 94/02516; U.S. Pat. No. 4,746,734; German Patent 294,267). Compositions of matter containing partially methylated derivatives of cyclodextrins can be synthesized under conditions of very low basicity, (minimal effective basicity). (See U.S. Pat. No. 5,681,828, U.S. Pat. No. 5,935,941; U.S. Pat. No. 6,001,821; World Intellectual Property Organization 92/22630.) The components of the latter mixtures are relatively few in number with substitution of the secondary hydroxyls predominating. Nevertheless, the mixtures prepared were found to exist in an amorphous state. Amorphous mixtures of partial 2-hydroxypropyl ethers of cyclodextrins (U.S. Pat. No. 5,096,893; U.S. Pat. No. 4,870,060) belong to this class and are produced using strong to moderately strong basicities.

Many chemically individual (and crystalline) cyclodextrin derivatives are known (A. R. Khan, et al., Chemical Reviews, 98, 1977–1996, 1998; A. R. Hedges, Chemical Reviews, 98, 2035–2044, 1998). Those of significant use include maltosyl-beta-cyclodextrin, which is produced industrially by enzymatic reaction (U.S. Pat. No. 4,931,389), and heptakis(2,6-di-O-methyl)-beta-cyclodextrin produced by reaction in strongly basic medium in presence of barium salts (U.S. Pat. No. 4,542,211). From the multitude of research generated compounds made by methods not suited for scale up, several chemically individual and crystalline methyl and 2-hydroxypropyl ethers of beta-cyclodextrin are known (K. Takeo et al., Die Starke 28, 226–227, 1976; K. Takeo et al., Carbohydrate Research, 187, 203–221, 1989; C. T. Rao et al., Journal of Organic Chemistry, 56, 1327–1329, 1991; J. Jindrich et al., Carbohydrate Research, 266, 75–80, 1995). It was believed that the crystallinity of these particular compounds was dependent on their being present as separate distinct entities, not as mixtures. The possibility of the existence of a crystalline lattice, which can accommodate a number of cyclodextrin derivatives of the kind described herein was not considered.

Water-soluble cyclodextrin derivatives, after their preparation, have to be separated from water-soluble by-products, i.e., inorganic salts and small molecular weight organic compounds. This has been done by diffusion-based processes, by demineralization with ion exchange resins, or by precipitation with organic solvents (A. R. Hedges, Chemical Reviews, 98, 2035–2044, 1998). In diffusion-based processes, the aqueous solution of product and by-products is brought into contact with a semi-permeable membrane which may, depending on the method of manufacture, permit only molecules that are smaller than those of the product to diffuse through. The other side of the membrane is in contact with water, or at least is covered by water. The smaller molecules of the by-product flow through the membrane to the aqueous side, where their concentration is lower. Molecules of water, since they obey the same physical law, flow in the opposite direction. This water flow leads to undesirable dilution of the desired product and can be prevented, or even reversed, by an increase of pressure on the product/by-product side. In the dialysis process, as used in the laboratory, the pressure on the product/by-product side of the membrane is not large enough to prevent fully the flow of water across the membrane into the desired product. Sturdy instrumentation that permits pressure large enough to prevent that flow or even reverse it, is known as reverse osmosis instrumentation. Use of reverse osmosis instrumentation to remove specific by-products, but not calcium salts, from cyclodextrin derivatives was disclosed in U.S. Pat. No. 5,831,081.

SUMMARY OF THE INVENTION

The present invention provides means for making certain mixtures of cyclodextrin derivatives that can be separated into crystalline and noncrystalline (amorphous) components. The crystallization does not lead to separation of individual compounds. Rather, both the crystalline and non-crystalline components remain as mixtures of more than one compound. Crystalline and amorphous states are associated with different and distinct advantages. The present invention enables access to compositions having the advantages of both states from one reaction product. The data provided herein show that components of both crystalline and amorphous states may have similar numbers of substituents per cyclodextrin residue: it is the position of substituents that is critical for determining crystallization properties of particular cyclodextrin products.

The invention provides compositions of matter comprising mixtures of partial ethers of parent cyclodextrins containing a crystalline component and an amorphous component wherein the crystalline component is comprised of cyclodextrins wherein total ether substituents are less than two times the number of glucose residues. It is possible to obtain therefrom a crystalline component containing mixtures of partial ethers of cyclodextrins. These crystalline cyclodextrins can form new, useful inclusion complexes with active agents such as drugs, agricultural chemicals, reaction agents, cosmetics, dyes and catalysts.

DETAILED DESCRIPTION OF THE INVENTION

During methylation of beta-cyclodextrin using calcium hydroxide (i.e., base of minimal effective basicity) and low temperature, it was observed that crystals started to separate from concentrated solutions of the product. The crystalline phase thus obtained contained, in a single crystal, a multitude of chemically individual compounds, which among other aspects, differed by the number of methyls per molecule. This set apart the present composition of matter from compositions of previous art, in which existence of the single crystalline phase was associated with chemical individuality. Using these crystals as a seed, crystallization of other mixtures of partial methyl ethers of beta-cyclodextrin made in conditions of minimal effective basicity was possible. Crystalline phases were eventually obtained, but with much lower yields, from the corresponding derivatives of alpha-and gamma-cyclodextrin and from similar mixtures of partial hydroxypropyl ethers of beta-cyclodextrin, partial carboxymethyl ethers of beta-cyclodextrin and partial ethyl ethers of beta-cyclodextrin. In all of these cases, including partial methyl ethers of beta-cyclodextrin, reaction products contained both crystalline and amorphous phases.

Crystalline mixtures of partial methyl ethers of cyclodextrins of the present invention can be made in forms which vary in extent of overall substitution, in ease of crystallization, in solubility in water and in capacity to act as hosts in formation of inclusion complexes. Noncrystalline components of the compositions of matter of the present invention can also vary in degree of substitution and in their capacity to act as hosts.

The majority of cyclodextrin derivatives in use at present are amorphous mixtures. From the user's point of view, the main advantage of amorphous character of a mixture is that it confers to its inclusion complexes high solubility. The principal disadvantage of the amorphous state of a mixture is that untoward properties of the cyclodextrin components are, given time, fully manifested. Components of amorphous mixtures of partial methyl and hydroxypropyl ethers of cyclodextrins, which have a high degree of substitution, are hygroscopic. This invariably leads to stickiness of the whole mixture and to difficulties in storage and mechanical processing. Another disadvantage is that the word "crystalline" nearly universally conveys feeling of the purity; the word "amorphous" conveys the very opposite.

From the view of producer, the amorphous state requires that the crude reaction product must fulfill all the purity criteria required in final products. None of the purification methods for use on amorphous compositions are sufficiently cost effective for large-scale production. Crystalline materials, on the other hand, can be inexpensively recrystallized until the desired purity is achieved. The effectiveness of recrystallization is well recognized by regulatory agencies. (Manufacture of pharmaceutical grades of glucose and sucrose serve as examples.)

In Example 1, a procedure is described for making the crystalline partial methyl ethers of cyclodextrin using calcium hydroxide. Results show that the level of methylation of the crystalline components of the mixture do not differ greatly in number of methyl groups per molecule from those of amorphous components left in mother liquors. The ease and rapidity with which crystallization of the purified multicomponent mixture of partial methyl ethers of beta-cyclodextrin occurs suggests that its components are isomorphous. In Example 1, it also is shown that reverse osmosis instrumentation can be used effectively to isolate the product.

In Example 2, it is shown that the crystalline phase can be isolated from many reaction products of cyclodextrins. The products of methylation of beta-cyclodextrin made using mild bases in addition to calcium hydroxide may also be used in compositions to provide crystalline products, albeit with lower yields. Results in Example 2 also show that a number of additional factors impact yields of the crystalline component of the mixtures. Yields of the crystalline component are improved when lower reaction temperatures and less alkylation agent are used. These factors are expected to impact crystallization potential since they diminish the number and variety of individual chemical compounds present in the reaction product. Surprisingly, there was a difference between alkylating agents, dimethyl sulfate giving higher yields than methyl iodide. Yields of the crystalline component were increased when barium ions were added to the reaction mixture. Partial methyl ethers of beta-cyclodextrin were found to crystallize much better than those of alpha- and gamma-cyclodextrins. Changes in size of substituent (e.g., moving from the smaller methyl to the larger ethyl, carboxymethyl, 2-hydroxypropyl) substituents also decreased the ability of derivatives to form crystals. When 2-hydroxypropyl groups were tested, only components with two or fewer hydroxypropyl groups per cyclodextrin residue were detectable in crystals obtained.

Results in Example 3 document the structure of components of the crystalline phase and described some of its properties. A single crystal of a methylation product of beta-cyclodextrin was grown large enough for all required analyses. That crystal contained 17% of water of crystallization. Analysis of the substitution pattern (J. Reuben, Carbohydrate Research, 1986, 157, 201–213 and references therein) of this crystal revealed that the only methylation which occurred was that on OH-2 hydroxyls and not all of these were methylated. Mass spectrum of the same crystal documented that species from one to seven methyl groups per molecule were present. These results prove that the crystal is formed by isomorphous 2-O-oligomethyl beta-cyclodextrins. The absence of methylation on OH-6 hydroxyls also was documented chemically as shown by ease of formation of tertiary butyl ethers. Average number of methyls per molecule of the crystalline product can be manipulated by changes in amount of methylation agent used in preparation. Increase in that number is accompanied by an increase in solubility in water. When amounts of methylation agent were increased substantially, species with more methyls than seven per molecule could be detected in crystalline phase by mass spectrometry. Results in Example 3 also show that the compositions of matter of the present invention are different from any partial methyl ethers of cyclodextrin of previous art.

In Example 4, it is shown that both the crystalline and amorphous components of partial methyl ethers of cyclodextrin preparations are good solubilizers. Hydrocortisone, a drug that has commonly been used as comparison standard in this field, was solubilized more efficiently using compositions of the invention than by currently available cyclodextrin compositions. Hydrocortisone was shown to increase the solubility of crystalline partial methyl ethers of beta-cyclodextrin in water. Example 4 also describes methods that can be used to produce liquid or solid pharmaceutical formulations. The same methods are expected to have applications for preparation of personal care products and formulations used in agriculture.

Results in Example 5 show that the crystalline mixtures containing partial methyl ethers of cyclodextrin are of low toxicity and that biological activity of guests is unaffected when using such cyclodextrin derivatives as hosts.

EXAMPLE 1

Preparation of Partly Crystalline Methyl Beta-Cyclodextrin

Calcium oxide, freshly made from calcium hydroxide (23.9 g), was added to water (400 ml) while cooling. Beta-cyclodextrin hydrate (80 g) was then added while stirring, followed by dropwise addition of dimethyl sulfate (27.8 ml), which took about two hours. Stirring at room temperature was continued for four days. The still alkaline reaction mixture was then saturated with carbon dioxide until pH decreased to 5–6. Thereafter, the suspension was boiled for a few minutes to expel carbon dioxide and methanol. After cooling the suspended calcium carbonate was filtered off and the clear filtrate dialyzed against distilled water. In this particular dialysis, the mechanical pressure on the product/by-product side of the semipermeable membrane was not large enough to prevent inflow of water. Nevertheless, by a moderate increase of reverse pressure, it was possible to decrease inflow, while the removal of calcium salts was not impeded. It also was possible to obtain separation using a centrifugal filter unit equipped with an ultrafiltration membrane of nominal molecular weight cutoff of 3000 D. Although this cutoff was higher than the molecular weight of the product and washing washing was necessary, product was obtained. Consequently, use of commercially available instrumentation, would be appropriate for removal of calcium salts (e.g., methylsulfate, sulfate, bicarbonate and carbonate) which represent the majority of by-products present in the reaction product.

The dialyzed solution of the product can be further purified by treatment with a solution of sodium carbonate until no calcium carbonate separated. The suspension was filtered and the filtrate was treated with demineralizing ion exchange resin, filtered again and evaporated in vacuo to yield 59.7 g of white mass. This white mass was dissolved in boiling water (60 ml) and left to crystallize. Crystals thus obtained were again recrystallized at 1:1 w/w (water to crystals), yielding 25.06 g of colorless needles. Mother liquors, when evaporated to dryness, yielded 30.19 g of white mass. Results of thin layer chromatography showed that crystals and mother liquors contain partial ethers of cyclodextrins that do not differ greatly in the number of methyl groups per molecule. Interestingly, crystals contained less of the beta-cyclodextrin and its monomethyl derivative than mother liquors. Neither the crystalline component, nor the component obtained by evaporating of the mother liquor, melted at less than 200 degrees centigrade.

EXAMPLE 2

Isolation of Crystalline Parts from Various Cyclodextrin Derivatives Prepared in Conditions of Minimal Effective Basicity Partial methyl ethers of beta-cyclodextrin (1 g), prepared in the conditions specified in Table 1, were dissolved in water (1 ml) at temperature of boiling water bath. If, upon cooling, crystals did not appear, the solution was seeded with crystals obtained in Example 1. After a week of standing at room temperature, the crystals were collected and weighed. Results in Table 1 show that the yield of crystals improves when methylation occurs at lower reaction temperatures and with use of less methylation agent. Mother liquors, when partially evaporated, yielded additional crystals. Beta W7 M1.8, a commercial noncrystalline derivative produced by Wacker Biochem Corp., was used as a control. (Beta W7 M 1.8 is not prepared in conditions of minimal effective basicity.) Hydroxypropyl beta-cyclodextrin mixtures prepared using calcium hydroxide at room temperature yielded crystalline components that contained di(2-hydroxypropyl)-beta-cyclodextrins in addition to the starting beta-cyclodextrin and mono(2-hydroxypropyl)- beta-cyclodextrins. This was established by thin layer chromatography. Carboxymethyl substituents may also be present on cyclodextrins in the crystalline component. This was established by alkylating beta-cyclodextrin using chloroacetic acid, 2 moles per mole of glucose residue and using calcium hydroxide as a base. Large crystals in low yield were obtained from the product. Crystalline partial ethyl ethers were obtained by alkylation of beta-cyclodextrin with ethyl iodide under conditions similar to those used in preparation of P264 in Table 1. Products of methylation of alpha- and gamma-cyclodextrins were made using calcium hydroxide. The product, when processed as described above, yielded only small amounts of fine particles, possibly microcrystals, under these conditions. This failure to provide larger crystals was probably due to the very high water solubility. When methanol-propanol mixtures were used, crystals were obtained. The crystallization occurred slowly. In all the cases, except with partial methyl ethers of beta-cyclodextrin, the yields of crystals were low. Nevertheless, some crystals were obtained. When conditions of minimal effective basicity were not used, no crystals resulted.

TABLE 1

Preparation and Crystallinity of Partial Methyl Ethers of Beta-Cyclodextrin

| Preparation | Base Used | Methylation Reagent, Moles per Mole of Glucose Residue | Reaction Temperature[1] | Crystalline Component (% of product) |
|---|---|---|---|---|
| P264 | Calcium Hydroxide | Dimethyl Sulfate, 0.5 Moles | Low | 55 |
| P258 | Calcium Hydroxide | Dimethyl Sulfate, 1 Mole | Low | 30 |
| P414 | Calcium Hydroxide | Dimethyl Sulfate, 1 Mole | Elevated | 24 |
| P164 | Calcium Hydroxide | Methyl Iodide, 1 Mole | Elevated | 16 |
| P165 | Calcium Hydroxide | Methyl Iodide, 1.8 Moles | Elevated | Negligible |
| P209 | Calcium Hydroxide[2] | Methyl Iodide, 2 Moles | Elevated | 11 |
| P162 | Calcium Hydroxide | Methyl Iodide, 4 Moles | Elevated | Negligible |
| P221 | Sodium Aluminate | Dimethyl Sulfate, 0.9 Moles | Elevated | 11 |
| P241 | Sodium Silicate | Dimethyl Sulfate, 0.9 Moles | Elevated | 3 |
| P224 | Sodium Stannate | Dimethyl Sulfate, 0.9 Moles | Elevated | 30 |
| P240 | Sodium Zincate | Dimethyl Sulfate, 0.9 Moles | Elevated | 7 |

TABLE 1-continued

Preparation and Crystallinity of Partial
Methyl Ethers of Beta-Cyclodextrin

| Preparation | Base Used | Methylation Reagent, Moles per Mole of Glucose Residue | Reaction Temperature[1] | Crystalline Component (% of product) |
|---|---|---|---|---|
| Beta W7 M1.8 | Sodium Hydroxide | Methyl Chloride, 2.8 Moles | 80° C. | None |

[1]Low reaction temperature denotes temperatures between 0 and 20 degrees of centigrade. Elevated temperature denotes that the reaction mixture was boiled under reflux.
[2]Barium chloride was added to the reaction mixture

EXAMPLE 3

Characterization of Crystalline Partial Methyl Ethers of Beta-Cyclodextrin

The crystalline component of P264 (Table 1), after drying at 100 degrees centigrade in vacuo to remove all of its cystallization in water, was soluble in water at room temperature to the concentration 15%; at temperature of a boiling water bath, the solubility was in excess of 50%. The moderate solubility of the crystalline component of P264 in water at room temperature is not a barrier to achieving a higher total concentration of that composition in the presence of a suitable drug, as is shown in Example 4. Crystals did not melt at temperatures of up to 200 degrees centigrade.

When a single crystal of P264 was hydrolyzed, only glucose and 2-O-methyl glucose were detected in hydrolyzate by $^{13}$C-N.M.R. (J. Reuben, Carbohydrate Research, 1986, 157, 201–213). Mass spectrum (FAB in positive ionization mode) of the same crystal documented the following composition: Beta cyclodextrin not detectable; less than 1% of molecules had one methyl, 3% two methyls, 15% three methyls, 41% four methyls, 25% five methyls, 11% six methyls, 3% seven methyls and less than 1% eight methyls.

The absence of substitution on primary hydroxyls (OH-6) in P264 also was documented chemically. A sample of it was dissolved in trifluoracetic acid and saturated with isobutylene. This reaction is known to introduce tertiary butyl groups onto primary hydroxyls. The product isolated form this reaction mixture indeed contained tertiary butyl groups.

The crystalline component of P258 (Table 1), after drying at 100 degrees centigrade in vacuo, was soluble in water at room temperature to the concentration 29%; at temperature of boiling water bath, the solubility was in excess of 50%. Crystals did not melt at temperatures of up to 200 degrees centigrade. Mass spectrum (FAB in positive ionization mode) showed that from di- to deca-methyl species were present with heptamethyl beta-cyclodextrin in the largest quantity. 13C-N.M.R. data shows that about 76% of OH-2 were converted to methyl ether groups (calculated from intensities of C-1 signals).

These results show clear differentiation between the compositions of the present invention and of the previously known partial methyl ethers of cyclodextrins, both amorphous and crystalline. The compositions of matter of the present invention differ from all previously described amorphous materials, since a crystalline state exists therein and a phase containing the crystalline state can be obtained therefrom. It differs from the known crystalline heptakis(2,6-di-O-methyl)-beta-cyclodextrin, which contains 14 methyls per molecule, both in terms of number of methyls per moleucle and in effects of temperature on solubility in water (see Y. Kubota et al., Carbohydrate Research, 192, 159–166, 1989).

EXAMPLE 4

Solubilizing Potency of Partial Methyl Ethers of Beta-Cyclodextrins and Their Use in Pharmaceutical Formulations Solubilization potency of cyclodextrin derivatives was compared through measurement of the solubility of hydrocortisone in 5%(w/w) aqueous solutions of the said derivatives, which in the case of the crystalline components of P264 and P258 (Table 1), were used without heat drying. The results are shown in Table 2.

TABLE 2

Solubilizing Potency of Various Derivatives of Beta-Cyclodextrins

| Cyclodextrin Derivative | Solubility Of Hydrocortisone (mg/ml) |
|---|---|
| Crystalline Component of P264 | 10.0 |
| Crystalline Component of P258 | 10.9 |
| Hydroxypropyl Beta-Cyclodextrin, Commercial | 5.1 |
| Beta W7 M1.8, Commercial | 7.1 |
| Heptakisdimethylbetacyclodextrin, Commercial | 8.8 |

The concentration limits to which solubilization power of the crystalline component of P264 can be utilized were investigated in an experiment in which an excess of hydrocortisone was added to the aqueous system which contained more of the crystalline component of P264 than it could dissolve. The results in Table 3 show that, in these conditions, hydrocortisone solubilized additional amounts of the crystalline component of P264. In other words, the stability and solubility of the inclusion complex is high enough to lead to dissolution of all host available. Results in Table 3 also show that the amorphous component of P264, the mother liquors of P264, is a powerful solubilizer as well.

TABLE 3

Solubility of Hydrocortisone (mg/ml)

| Cyclodextrin Derivative | Amount of Cyclodextrin Derivative Added to Water | | |
|---|---|---|---|
| | 5% | 10% | 20% |
| Crystalline Component of P264 | 10.0 | 21.5 | 43.9 |
| Amorphous Component of P264 | 11.8 | 25.6 | 42.5 |
| Hydroxypropyl Beta-Cyclodextrin, Commercial | 5.1 | | |

A solution of a drug suitable for topical or parenteral uses was made by adjusting the hydrocortisone solution made as in Table 2 to isotonicity by addition of sodium chloride. The solution thus made did not deteriorate during storage at room temperature for several months.

The solutions of hydrocortisone and the crystalline components of P264 and P258, upon slow evaporation, yield glassy materials, which in some instances were bordered with traces of apparently crystalline phase products. The inclusion complex of crystalline partial methyl ethers of beta-cyclodextrin is very water soluble. However, with perseverance the crystalline state could be induced. Tablets suitable for oral or buccal use were made by direct compression of the residue after evaporation of the above solution of hydrocortisone inclusion complexes. These tablets dissolved clearly and fully within 2–3 minutes in water.

EXAMPLE 5

Bioeffects and Toxicity Issues

The solutions of the crystalline partial methyl ethers of beta-cyclodextrin described above were nontoxic to mice when given as the only source of liquids at 2% concentration for two days. These solutions have a mildly sweet taste without aftertaste. When given by intraperitoneal injection, no toxic effects to mice were seen at doses to 6 g per kg; the first toxic effects were seen at 7 g per kg doses.

To demonstrate that a drug included in crystalline partial methyl ethers of beta-cyclodextrin retains its potency, the blanching test was used (McKenzie, Archives of Dermatology, 86, 91–94, 1962). An aqueous solution (25 microliters) containing hydrocortisone (8 mg/ml) and crystalline partial methyl ethers of beta-cyclodextrin (5%) was applied to the skin of the human forearm. After drying of the droplet by warm air, the test area was covered by an occlusive bandage overnight. The skin area to which the solution was applied was then evaluated for signs of blanching comparing the treated areas of both untreated skin (negative control) and skin to which a hydrocortisone solution (1%) in ethanol had been applied in a similar manner (positive control, known to produce blanching). The tested solution produced blanching surpassing that of the positive control.

I claim:

1. A composition comprising a crystalline component of mixtures of partial ethers of parent cyclodextrins wherein total ether substituents are less than two times the number of glucose residues.

2. The composition of claim 1 wherein the ethers of cyclodextrins have formed inclusion complexes.

3. The composition of claim 2 wherein the ethers of cyclodextrins have formed inclusion complexes with a drug.

4. The composition of claim 2 wherein the ethers of cyclodextrins have formed inclusion complexes with an agricultural chemical.

5. The composition of claim 2 wherein the ethers of cyclodextrins have formed inclusion complexes with a catalyst.

6. The composition of claim 2 wherein the ethers of cyclodextrins have formed inclusion complexes with a dye.

7. A composition comprising mixtures of partial ethers of parent cyclodextrins containing a crystalline component and a simultaneously produced non-crystalline component wherein the crystalline component is comprised of mixtures of partial ethers of parent cyclodexrins wherein total ether substituents replacing hydroxyl groups of the parent cyclodextrins are less that two times the number of glucose residues.

8. The composition of claim 7 wherein the parent cyclodextrin is a beta-cyclodextrin wherein there are no more than 13 ether substituents replacing hydroxyl groups on the cyclodextrin molecule.

9. The composition of claim 8 wherein the ether moieties are methyl ethers.

10. The composition of claim 7 wherein the ether moieties replacing the hydroxyl substituents on the parent cyclodextrin are methyl ethers.

11. The composition of claim 10 wherein the parent cyclodextrin is a beta-cyclodextrin.

12. The composition of claim 7 wherein the ethers of cyclodextrins have formed inclusion complexes.

13. The composition of claim 12 wherein the ethers of cyclodextrins have formed inclusion complexes with a drug.

14. The composition of claim 12 wherein the ethers of cyclodextrins have formed inclusion complexes with an agricultural chemical.

15. The composition of claim 12 wherein the ethers of cyclodextrins have formed inclusion complexes with a catalyst.

16. The composition of claim 12 wherein the ethers of cyclodextrins have formed inclusion complexes with a dye.

* * * * *